US012318511B2

(12) United States Patent
Farrell et al.

(10) Patent No.: US 12,318,511 B2
(45) Date of Patent: *Jun. 3, 2025

(54) HYGIENIC MEDICAL DEVICES HAVING HYDROPHILIC COATINGS AND METHODS OF FORMING THE SAME

(71) Applicant: Hollister Incorporated, Libertyville, IL (US)

(72) Inventors: David J. Farrell, Ballina (IE); John P. O'Mahony, Ardnacrusha (IE); James J. Fitzpatrick, Ballina (IE); Padraig M. O'Flynn, Ballina (IE); Paul C Fletter, Mt. Prospect, IL (US); William K. Arnold, Gurnee, IL (US); John T. Clarke, Galway (IE); Adam J. Foley, Swords (IE); Malford E. Cullum, Grayslake, IL (US)

(73) Assignee: Hollister Incorporated, Libertyville, IL (US)

( * ) Notice: Subject to any disclaimer, the term of this patent is extended or adjusted under 35 U.S.C. 154(b) by 911 days.

This patent is subject to a terminal disclaimer.

(21) Appl. No.: 17/495,061

(22) Filed: Oct. 6, 2021

(65) Prior Publication Data
US 2022/0023508 A1 Jan. 27, 2022

Related U.S. Application Data

(63) Continuation of application No. 16/317,724, filed as application No. PCT/US2017/041924 on Jul. 13, 2017, now Pat. No. 11,167,064.

(60) Provisional application No. 62/362,409, filed on Jul. 14, 2016.

(51) Int. Cl.
A61L 29/08 (2006.01)
A61L 29/00 (2006.01)
A61L 29/16 (2006.01)
A61L 31/00 (2006.01)
A61L 31/10 (2006.01)
A61L 31/16 (2006.01)

(52) U.S. Cl.
CPC ........... *A61L 29/085* (2013.01); *A61L 29/005* (2013.01); *A61L 29/08* (2013.01); *A61L 29/16* (2013.01); *A61L 31/005* (2013.01); *A61L 31/10* (2013.01); *A61L 31/16* (2013.01); *A61L 2300/232* (2013.01); *A61L 2300/254* (2013.01); *A61L 2400/10* (2013.01)

(58) Field of Classification Search
CPC ........ A61L 29/085; A61L 29/08; A61L 29/16; A61L 31/005; A61L 29/005; A61L 31/10; A61L 31/16; A61L 2400/10; A61L 2300/254; A61L 2300/232
See application file for complete search history.

(56) References Cited

U.S. PATENT DOCUMENTS

| | | |
|---|---|---|
| 3,566,874 A | 3/1971 | Shepherd |
| 4,585,666 A | 4/1986 | Lambert |
| 4,708,765 A | 11/1987 | Newman et al. |
| 4,874,373 A | 10/1989 | Luther |
| 4,874,690 A | 10/1989 | Goodrich, Jr. |
| 4,925,668 A | 5/1990 | Khan |
| 4,950,256 A | 8/1990 | Luther |
| 4,990,357 A | 2/1991 | Karakelle |
| 5,015,238 A | 5/1991 | Solomon |
| 5,019,096 A | 5/1991 | Fox, Jr. |
| 5,041,100 A | 8/1991 | Rowland |
| 5,061,424 A | 10/1991 | Karimi |
| 5,064,415 A | 11/1991 | Walder |
| 5,077,352 A | 12/1991 | Elton |
| 5,091,205 A | 2/1992 | Fan |
| 5,272,012 A | 12/1993 | Opolski |
| 5,295,978 A | 3/1994 | Fan |
| 5,322,659 A | 6/1994 | Walder |
| 5,328,954 A | 7/1994 | Sarangapani |
| 5,558,900 A | 9/1996 | Fan |
| 5,620,738 A | 4/1997 | Fan |
| 5,688,855 A | 11/1997 | Stoy |
| 5,712,229 A | 1/1998 | Hopkins |
| 5,731,087 A | 3/1998 | Fan |
| 5,752,941 A | 5/1998 | Romano |
| 5,772,640 A | 6/1998 | Modak |
| 5,869,127 A | 2/1999 | Zhong |
| 5,877,243 A | 3/1999 | Sarangapani |
| 5,984,965 A | 11/1999 | Knapp |
| 6,054,504 A | 4/2000 | Dalla Riva Toma |
| 6,087,415 A | 7/2000 | Vanderlaan |
| 6,107,416 A | 8/2000 | Patnaik |
| 6,221,425 B1 | 4/2001 | Michal et al. |
| 6,224,579 B1 | 5/2001 | Modak |
| 6,238,799 B1 | 5/2001 | Opolski |
| 6,329,488 B1 | 12/2001 | Terry |

(Continued)

FOREIGN PATENT DOCUMENTS

| | | | |
|---|---|---|---|
| CN | 104857573 | * | 8/2015 |
| EP | 443809 A2 | | 8/1991 |

(Continued)

OTHER PUBLICATIONS

CN 104857573 translated (2015).*
International Search Report and Written Opinion dated Apr. 3, 2018 for Internation Application No. PCT/US2017/041924.
Mistry, S. "Use of Hydrophilic-Coated Urethral Catheters in Management of Acute Urinary Retention", Urology 70, pp. 25-27 (2007).
Ghelzelbash, G. R., "Comparative inhibitory effect of xylitol and erythritol on the growth and biofilm formation of oral streptocci", African Journal of Mircobiology Research, 6(20), pp. 4404-4408, (2012).
Thallinger, B. Functionalization of Catheters with Antimicrobial Enzymes, Dissertation, Institut fur Umweltbiotechnologie Universitat fur Bodenkultur Wien (2015).

(Continued)

Primary Examiner — Shirley V Gembeh
(74) Attorney, Agent, or Firm — Cook Alex Ltd.

(57) ABSTRACT

Hygienic Hydrophilic coatings, hydrophilic coating formulations and wetting fluids that include an anti-infective agent.

23 Claims, 3 Drawing Sheets

(56) References Cited

U.S. PATENT DOCUMENTS

| | | |
|---|---|---|
| 6,340,465 B1 | 1/2002 | Hsu |
| 6,436,422 B1 | 8/2002 | Trogolo |
| 6,468,521 B1 | 10/2002 | Pedersen |
| 6,582,715 B1 | 6/2003 | Barry |
| 6,596,402 B2 | 7/2003 | Soerens |
| 6,716,895 B1 | 4/2004 | Terry |
| 6,808,738 B2 | 10/2004 | DiTizio |
| 6,866,859 B2 | 3/2005 | Trogolo |
| 6,876,887 B2 | 4/2005 | Okuzumi |
| 7,008,979 B2 | 3/2006 | Schottman |
| 7,220,491 B2 | 5/2007 | Rouns |
| 7,402,318 B2 | 7/2008 | Morris |
| 7,571,804 B2 | 8/2009 | Kjellmann Bruun |
| 7,749,203 B2 | 7/2010 | Bucay-Couto |
| 7,794,490 B2 | 9/2010 | King |
| 7,807,750 B2 | 10/2010 | Taton |
| 7,820,734 B2 | 10/2010 | McGhee |
| 7,863,264 B2 | 1/2011 | Vange |
| 7,955,636 B2 | 6/2011 | Terry |
| 8,053,078 B2 | 11/2011 | Hu |
| 8,071,156 B2 | 12/2011 | Weber |
| 8,080,028 B2 | 12/2011 | Cagle |
| 8,101,200 B2 | 1/2012 | Whitbourne |
| 8,137,735 B2 | 3/2012 | Wang |
| 8,172,395 B2 | 5/2012 | Carney |
| 8,173,151 B2 | 5/2012 | Szycher |
| 8,328,792 B2 | 12/2012 | Nishtala |
| 8,414,547 B2 | 4/2013 | DiFiore |
| 8,512,736 B2 | 8/2013 | Chudzik |
| 8,709,470 B2 | 4/2014 | Bee Eng Mary |
| 8,747,882 B2 | 6/2014 | Utas |
| 8,795,573 B2 | 8/2014 | Bracken |
| 8,932,662 B2 | 1/2015 | Nielsen |
| 8,956,682 B2 | 2/2015 | Lockwood |
| 8,998,882 B2 | 4/2015 | Knapp |
| 9,028,858 B2 | 5/2015 | Nielsen |
| 9,033,149 B2 | 5/2015 | Terry |
| 2002/0045049 A1 | 4/2002 | Madsen |
| 2002/0120333 A1 | 8/2002 | Keogh |
| 2002/0150549 A1 | 10/2002 | Vogt |
| 2003/0144362 A1 | 7/2003 | Utterberg |
| 2003/0194480 A1 | 10/2003 | Leukel et al. |
| 2004/0030301 A1 | 2/2004 | Hunter |
| 2004/0214809 A1 | 10/2004 | Capelli |
| 2005/0008676 A1 | 1/2005 | Qiu |
| 2005/0137582 A1 | 6/2005 | Kull-Osterlin |
| 2005/0186427 A1 | 8/2005 | Gatto |
| 2006/0045899 A1 | 3/2006 | Sarangapani |
| 2006/0118121 A1 | 6/2006 | Martens |
| 2007/0026043 A1 | 2/2007 | Guan |
| 2007/0048249 A1 | 3/2007 | Youngblood |
| 2007/0166344 A1 | 7/2007 | Qu |
| 2008/0085949 A1 | 4/2008 | McGhee |
| 2008/0125513 A1 | 5/2008 | Kristiansen |
| 2008/0306455 A1 | 12/2008 | Dias et al. |
| 2009/0054876 A1 | 2/2009 | Borodulin |
| 2009/0099531 A1 | 4/2009 | Griesbach, III |
| 2009/0099532 A1 | 4/2009 | Cuevas |
| 2009/0176183 A1 | 7/2009 | Conrad |
| 2009/0214652 A1 | 8/2009 | Hunter et al. |
| 2009/0240214 A1 | 9/2009 | Conway |
| 2009/0252699 A1 | 10/2009 | Kocher |
| 2009/0252804 A1 | 10/2009 | Koecher |
| 2009/0253826 A1 | 10/2009 | Kocher |
| 2009/0280153 A1 | 11/2009 | Hunter et al. |
| 2009/0281635 A1 | 11/2009 | Li |
| 2010/0074932 A1 | 3/2010 | Talsma |
| 2010/0086580 A1 | 4/2010 | Nyman |
| 2010/0100009 A1 | 4/2010 | Nielsen |
| 2010/0113871 A1 | 5/2010 | Dias et al. |
| 2010/0198195 A1 | 8/2010 | Nishtala |
| 2010/0234945 A1 | 9/2010 | O-Leary |
| 2010/0258568 A1 | 10/2010 | Frederiksen |
| 2011/0060070 A1 | 3/2011 | Dias et al. |
| 2011/0120892 A1 | 5/2011 | Frederiksen |
| 2011/0123475 A1 | 5/2011 | Dias et al. |
| 2011/0150961 A1 | 6/2011 | Perry |
| 2011/0152843 A1 | 6/2011 | Wedlin |
| 2011/0301553 A1 | 12/2011 | Goral |
| 2012/0168324 A1 | 7/2012 | Carleo |
| 2012/0179144 A1 | 7/2012 | Carleo |
| 2012/0289942 A1 | 11/2012 | Becker |
| 2012/0316515 A1 | 12/2012 | Terry |
| 2012/0328713 A1 | 12/2012 | Olson |
| 2013/0245568 A1 | 9/2013 | Kerr |
| 2013/0255061 A1 | 10/2013 | Burkholz |
| 2013/0310764 A1 | 11/2013 | Burkholz |
| 2013/0323291 A1 | 12/2013 | Li |
| 2014/0178447 A1 | 6/2014 | Modak |
| 2015/0018431 A1 | 1/2015 | Zeng |
| 2015/0079144 A1 | 3/2015 | Hoang |
| 2015/0182673 A1 | 7/2015 | Delaney |
| 2015/0314103 A1 | 11/2015 | Hannon |
| 2015/0320971 A1* | 11/2015 | Leeflang ............... A61L 29/14 427/2.3 |
| 2016/0008517 A1 | 1/2016 | Burkholz |

FOREIGN PATENT DOCUMENTS

| | | |
|---|---|---|
| EP | 590348 A1 | 4/1994 |
| EP | 592870 A1 | 4/1994 |
| EP | 593284 A1 | 4/1994 |
| EP | 761243 A1 | 3/1997 |
| EP | 799623 A2 | 10/1997 |
| EP | 1048304 A1 | 2/2000 |
| EP | 2468319 A1 | 6/2012 |
| WO | WO 1989/003232 | 4/1989 |
| WO | WO 1992/019289 | 11/1992 |
| WO | WO 1996/023428 | 8/1996 |
| WO | WO 1998/058988 | 12/1998 |
| WO | WO 1998/058990 | 12/1998 |
| WO | WO 2000/023124 | 4/2000 |
| WO | WO 2000/044414 | 8/2000 |
| WO | WO 2000/064506 | 11/2000 |
| WO | WO 2001/036008 | 5/2001 |
| WO | WO 2011/011023 | 1/2011 |
| WO | WO 2011/088347 | 7/2011 |
| WO | WO 2013098188 * | 7/2013 |
| WO | WO-2013098188 A1 * | 7/2013 ........ A61M 25/0017 |
| WO | WO 2014/092660 | 6/2014 |
| WO | WO 2014/138885 | 9/2014 |
| WO | WO 2016/004366 | 1/2016 |

OTHER PUBLICATIONS

Lobo, et al., "Free radicals, antioxidants, and functional foods: Impact on human health", Pharmacogn Rev., 4(8), pp. 118-126, (2010).

Rodoni, et al., "The Detection of Dasheen Mosaic Virus Using the Enzyme-Lined immunosorbent Assay (Elisa)", Acta Hortic. 234, pp. 281-288 (1988).

Lopez, et al., "Biofunactionalization of Silicone Polymers Using Poly(amidoamine) Dendrimers and a Mannose Derivative for Prolonged Interference Against Pathogen Colonization", Biomaterials 32, pp. 4336-4346 (2011).

European Search Report Dated Feb. 21, 2022 for European Application No. EP21211920.

* cited by examiner

HYGIENIC MEDICAL DEVICES HAVING HYDROPHILIC COATINGS AND METHODS OF FORMING THE SAME

The present application is a continuation of U.S. Nonprovisional application Ser. No. 16/317,724, filed Jan. 14, 2019, which is the U.S. National Stage Application of PCT Application No. PCT/US2017/041924, filed Jul. 13, 2017, which claims the benefit of and priority to U.S. Provisional Patent Application No. 62/362,409, filed Jul. 14, 2016, the disclosures of which are incorporated herein by reference.

TECHNICAL FIELD

The present disclosure generally relates to hygienic medical devices including a hydrophilic coating and, more particularly, to coating formulations for preparing hygienic coatings, hydrophilic coatings and lubricious coatings that include anti-infective agents and methods of forming such coatings. The present disclosure also relates to wetting fluids that contain anti-infective agents.

BACKGROUND

It is desirable for medical devices that are inserted into the body to have a lubricated or lubricious outer surface to increase comfort of the patient during insertion into and/or removal from the body. Such devices may include, for example, urinary catheters, endoscopes, cardiovascular catheters, syringes, vascular stents, etc. One method for rendering the surface of a medical device lubricious is to coat at least the insertable portion of the medical device with a lubricious hydrophilic coating. An advantage associated with hydrophilic coatings is that the coatings become highly slippery or lubricous when wetted with a wetting fluid, such as saline or water. The high lubricity minimizes soft tissue damage and reduces overall discomfort during use of the medical device.

Although medical devices are typically prepared in sterile environments and are provided with safe handling instructions, the risk of bacterial contamination exists and is present whenever a medical device is inserted into a patient's body. For example, insertion of a urinary catheter into the urethra of a patient for draining a bladder inherently carries the risk of introducing bacteria and other contaminants into the urethra and bladder of the patient. The introduction of such contaminants into the urinary tract can lead to urinary tract and bladder infections. Such infections may result from the use of both intermittent and indwelling catheters. Additionally, it has been shown that some users who contract a urinary tract infection become more susceptible to recurrent urinary tract infections.

The use of intermittent catheters comprising anti-infective agents and/or agents that support bladder health can help prevent urinary tract infections and reduce the frequency of recurrent infection. Therefore, there is a need for medical devices which reduce the risk of associated infections.

SUMMARY

In one aspect, a hygienic medical device includes a surface and a coating disposed on the surface, wherein the coating includes a hydrophilic polymer and mannose.

In another aspect, a coating formulation for preparing a hydrophilic includes a liquid, a hydrophilic polymer and mannose.

In yet another aspect, a lubricous hydrophilic catheter assembly includes a gas impermeable and liquid impermeable package having a sealed cavity, a catheter having a hydrophilic coating, and a wetting fluid including a wetting agent and mannose.

In further aspect, a method of forming a hygienic medical device includes forming a hydrophilic coating on a medical device, wherein the hydrophilic coating includes a hydrophilic polymer and mannose.

In yet another aspect, a method of forming a hygienic medical device includes forming a hydrophilic coating on a medical device, and contacting the coating with a liquid including mannose to impregnate the hydrophilic coating with the mannose.

In another aspect, a hygienic medical device includes a surface, and a hydrophilic coating disposed on the surface, wherein the hydrophilic coating includes a hydrophilic polymer and honey.

In yet another aspect, a coating formulation for preparing a hydrophilic coating includes a liquid, a hydrophilic polymer, and honey.

In a further aspect, a coating formulation for preparing a hydrophilic coating includes a liquid, a hydrophilic polymer, C12 to C22 alcohol, and C12 to C22 alcohol ethoxylate.

In another aspect, a wetting fluid for wetting a hydrophilic coating includes a wetting agent, C12 to C22 alcohol, and C12 to C22 alcohol ethoxylate.

In yet another aspect, a lubricous hydrophilic catheter assembly includes a gas impermeable and liquid impermeable package having a sealed cavity, a catheter having a hydrophilic coating, and a wetting fluid including a wetting agent, C12 to C22 alcohol and C12 to C22 alcohol ethoxylate.

In another aspect, a coating formulation for preparing a hydrophilic coating includes a hydrophilic polymer and an aromatic alcohol, such as but not limited to phenoxyethanol, benzyl alcohol and phenylethyl alcohol.

In yet another aspect, a wetting fluid for wetting a hydrophilic coating includes a wetting agent and an aromatic alcohol.

In another aspect, a lubricous hydrophilic catheter assembly includes a gas impermeable and liquid impermeable package having a sealed cavity, a catheter having a hydrophilic coating, and a wetting fluid comprising a wetting agent and an aromatic alcohol.

DETAILED DESCRIPTION

Figure 1:
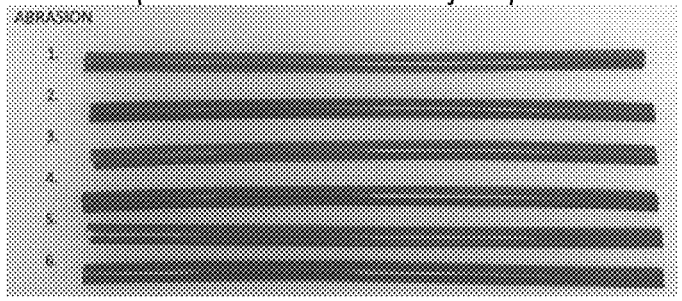
FIGS. 1 and 2 are photographs of catheter tubes showing the visual results of the dye uptake tests of Top Coat 1.

The present disclosure relates to formulations for forming hygienic hydrophilic coatings, hygienic lubricious coatings, medical devices including the aforementioned coatings and methods of forming such coatings. The present disclosure also discloses anti-infective additives and wetting fluids that impart anti-infective properties to hydrophilic coatings. The coatings, medical devices including such coatings, anti-infective additives and wetting fluids may be used in several different applications. For example, the coatings may be used to ease insertion of the medical device into various types of body cavities and lumens, while at the same time providing an anti-infective effect. The medical devices may be, for example, those which are configured for insertion into a lumen of a human body, such as the urethra, fallopian tubes, nasal passages, blood vessels or esophagus. Such medical devices may include, but are not limited to, urinary and vascular catheters and endoscopes. While the subject matter disclosed herein may be described relative to urinary catheters, the subject matter is not limited to such and such subject matter may apply to other suitable medical devices as well.

Urinary catheters typically include an elongated tube or catheter shaft having an insertable portion that is inserted through the urethra and into the bladder to drain urine therefrom. The catheter tube may include a proximal insertion end portion that is inserted through the urethra and into the bladder. The proximal end portion may have drainage eyes or holes that allow urine to drain from the bladder and through the catheter tube. The catheter tube also includes a distal end portion that may have a drainage element, such as a funnel, associated therewith to drain the urine into a collection container, such as a toilet or waste collection bag.

The elongated catheter tube may be made of any suitable materials, which are well known in the field. Such materials may include for example polyvinyl chloride, polyurethane, latex rubbers, silicone, thermoplastic elastomers (TPE), thermoplastic olefin (TPO), PEBAX etc. and copolymers and mixtures thereof.

A hygienic anti-infective hydrophilic coating is disposed on a surface of the catheter shaft. For example, the hydrophilic coating may be disposed on the insertable portion of the catheter shaft. The hydrophilic coating may include a hydrophilic polymer, anti-infective agent(s) and, optionally, other additives. The hydrophilic polymer may be any suitable hydrophilic polymer capable of providing hydrophilicity to the coating and/or lubriciousness when the coating is hydrated. The polymer may be synthetic or bio-derived and can be blends or copolymers of both. Suitable hydrophilic polymers include but are not limited to poly(lactams), for example polyvinylpyrrolidone (PVP), polyethylene oxide, polyurethanes, homo- and copolymers of acrylic and methacrylic acid, polyvinyl alcohol, polyvinyl ethers, maleic anhydride based copolymers, polyesters, vinyl amines, polyethylenimines, polyethylene oxides, poly(carboxylic acids), polyamides, polyanhydrides, polyphosphazenes, cellulosics, for example methyl cellulose, carboxymethyl cellulose, hydroxymethyl cellulose, and hydroxypropyl cellulose, heparin, dextran, polysaccharides, for example chitosan, hyaluronic acid, alginates, gelatin, and chitin, polyesters, for example polylactides, polyglycolides, and polycaprolactones, polypeptides, for example collagen and fibrins.

The anti-infective agents of the hydrophilic coating are agents that are capable of inhibiting the growth or migration of an infectious agent and/or are capable of killing an infectious agent. Such infectious agents may include bacteria, viruses, fungi and the like. The anti-infective agents of the hydrophilic coatings may include, for example, mannose, honey (natural or synthetic), C12 to C22 alcohol, C12 to C22 alcohol ethoxylate, aromatic alcohols, and/or polyols including sugar alcohols. Beneficially, such agents may also provide favorable osmolality without the need for additional tonicity agents.

Hydrophilic Coatings and Wetting Fluids Containing Mannose

Hygienic hydrophilic coatings of the present disclosure may include a hydrophilic polymer, mannose and, optionally, other additives and agents. As used herein, the term "mannose" includes D-mannose, L-mannose, oligomannose, polymannose and derivatives thereof.

The hygienic hydrophilic coating (in the dry state) may include
hydrophilic polymer(s) in an amount between about 80 wt % and about 99.9 wt % of the coating; and
mannose in an amount between about 0.1 wt % and about 20 wt % of the coating.

In one embodiment, the hygienic hydrophilic coating (in the dry state) may include
hydrophilic polymer(s) in an amount between about 90 wt % and about 99 wt % of the coating; and
mannose in an amount of about 1 wt % and about 10 wt %.

The hygienic hydrophilic coating may optionally include other agents or additives, such as organic acids, salts of organic acids, antioxidants and/or peroxide generating enzymes.

The organic acids may be, for example, citric acid, ascorbic acid (also an anti-oxidant), glycolic acid, acetic acid, butyric acid, formic acid, gluconic acid, lactic acid, malic acid, pyroglutamic acid, tartaric acid and succinic acid etc., glutaric acid, benzoic acid, polycarboxylic acid and mixtures thereof. The acid may be used to aid in maintaining a slightly acid pH in the coating and the surrounding environment, e.g., inside the package in which the device having the coating is stored. As explained in more detail below, the mannose may be catalyzed to produce peroxide, and a slightly acidic pH may help support peroxide stability in the coating composition and the surrounding environment. Depending on the application, it may be desirable to maintain a pH of approximately 4 to 8 in the coating and/or surrounding environment, preferably from approximately from 5 to 7, and more preferably approximately 5.5 to 6.5. The organic acids, or mixtures of organic acids, may be in an amount between about 0.01 wt % and about 8.0 wt % of the coating.

The antioxidants may be, for example, ascorbic acid, α-tocopherol, BHT-Alcohol and mixtures thereof. The antioxidants may be in an amount between about 0.01 wt % and about 1 wt % of the coating.

The peroxide generating enzyme may be any suitable enzyme that interacts with mannose to generate peroxide. Such enzymes may include, for example, an oxidoreductase such as glucose oxidase or peroxidase. The peroxidase may be, for example, lactoperoxidase. The peroxide generating enzyme may be in an amount that interacts with mannose to generate an effective amount of peroxide. For example, the enzyme may be in an amount sufficient to catalyze the mannose so as to produce an anti-infective amount of peroxide over the shelf life of the medical product. In one embodiment, the enzyme may be in an amount between about 0.0005 wt % and about 0.5 wt % of the coating. In another embodiment, the enzyme may be below 0.01 wt %. In other embodiments, the enzyme could be between about could be 10 U active units per 100 grams dry weight of the other components of the coating and about 4000 U active units per 100 grams dry weight.

When a peroxide generating enzyme, such as glucose oxidase, is included in the coating, such enzyme may catalyse a suitable substrate (e.g. mannose) to generate hydrogen peroxide. The amount of peroxide generating enzyme may be sufficient so that the catalyzation may generate peroxide steadily over a relatively long period of time, resulting in a continuous release of peroxide that can provide anti-infective protection during storage and use of the catheter.

The hydrophilic coating containing mannose may be formed from a hydrophilic coating formulation, such as a solution or dispersion, containing the hydrophilic polymer(s), mannose and, optionally, other agents/additives. The hydrophilic coating formulation may be applied to the catheter shaft by, for example, dip coating, spraying, painting or any other suitable coating procedure. Depending on the desired coating, the coating formulation may then be dried and/or cured to form the hydrophilic coating on the catheter. The hydrophilic coating may be formed directly on the surface of the catheter shaft. Alternatively, a base/tie coating layer may first be formed on the surface of catheter shaft, and then the hydrophilic coating may be formed on the base layer. In one embodiment, the base coat layer and formulation may include a hydrophilic polymer(s). The base coat layer may have good adhesion to both the surface of the catheter shaft and hydrophilic coating.

In one embodiment, the hydrophilic coating formulation (in the liquid state) may include hydrophilic polymer(s) in an amount between about 0.9 wt % and about 20 wt % of the coating formulation;

mannose in an amount between about 0.1 wt % and about 5.0 wt % of the coating formulation; and solvent in an amount between about 75 wt % and about 99 wt % of the coating formulation.

The solvent may be, for example, water, ethanol, methanol or any combination thereof or any other suitable solvent.

The hydrophilic coating formulation may optionally also include an effective amount of a peroxide generating enzyme that is effective to catalyse the mannose in the coating to generate peroxide during storage and use. In one embodiment, the peroxide generating enzyme may be in an amount between about 0.0005 wt % and about 0.25 wt % of the coating formulation. In another embodiment, the enzyme may be below 0.01 wt %. In another embodiment, the enzyme could be between about 10 U active units per 100 grams dry weight and about 1400 U active units per 100 grams dry weight. The amount of enzyme may be sufficient to yield between about 10 mg/100 g background hydrogen peroxide in the coating over time and about 25 mg/100 g background hydrogen peroxide in the coating over time. In yet another embodiment, the peroxide generating enzyme may be in an amount between about 0.075 wt % and about 0.5 wt % of the coating formulation. In yet another embodiment, the amount of peroxide could be between about 15 U active units per 100 grams dry weight and about 2800 U active units per 100 grams dry weight.

The coating may also optionally include a curing agent, such as benzophenone. The curing agent may be in an amount between about 0.01 wt % and about 1.0 wt %. The coating formulation may also optionally include an organic acid in an amount between about 0.1 wt % and about 8.0 wt %, and/or an antioxidant in an amount between about 0.05 wt % and about 1.0 wt %. The coating formulation may also optionally include any other suitable agents/additives, such as plasticizers, humectants, compounds that aid in attachment of the coating to a surface, and/or polyelectrolytes.

In one embodiment, the coating formulation may include hydrophilic polymer(s), such as PVP, in an amount between about 0.9 wt % and about 20 wt % of the coating formulation;

mannose, such as a mixture of d-mannose and oligomannose, in an amount between about 0.1 wt % and about 5.0 wt % of the coating formulation;

a curing agent in an amount between about 0.1 wt % and about 1.0 wt % of the coating formulation;

a peroxide generating enzyme, such as glucose oxidase, in an amount between about 0.01 wt % and about 0.07 wt % of the coating formulation; or the enzyme may be below 0.01 wt %; or the enzyme between about 10 U active units per 100 ml solution) and about 1400 U active units per 100 ml solution; and a solvent in an amount between about 73 wt % and about 98.8 wt % of the coating formulation.

Once the coating is formed on the catheter, the catheter may be packaged in a catheter assembly for storage, distribution and use by the end-user. The catheter assembly may include a package that contains the catheter and a wetting fluid that wets the hydrophilic coating to render it lubricious. The wetting fluid may include any suitable wetting agent that wets the hydrophilic coating. The wetting agent may be for example, water or saline. The hydrophilic coated catheter may be packaged in contact with the wetting fluid or the package may include separate compartments for the catheter and the wetting fluid wherein the compartments are brought into communication during the manufacturing process or just prior to use by the user.

In one embodiment, the catheter assembly includes a package having therein a catheter including a hydrophilic coating that has a hydrophilic polymer(s), mannose and, optionally, any of the above-mentioned additives/agents. In another embodiment, the package includes therein a catheter having a hydrophilic coating that has a hydrophilic polymer, mannose, a peroxide generating enzyme and, optionally, any other of the above-mentioned additives/agents.

In yet another embodiment, the catheter within the package may include a hydrophilic coating that has a hydrophilic polymer and mannose and, optionally, any of the above-mentioned additives/agents. The package also includes a wetting fluid that includes a wetting agent, such as water or saline, and a peroxide generating enzyme. In this embodiment, when the wetting fluid wets the hydrophilic coating and enters the matrix of the hydrophilic coating, the peroxide generating enzyme will enter the matrix and catalyze the mannose to generate peroxide while the catheter is stored within the package and during use by the user.

In yet another embodiment, the catheter may include a hydrophilic coating that does not include any mannose when the coating is formed. Mannose may be introduced into the coating by contacting the coating with a fluid that includes mannose. Optionally, the fluid may also include a peroxide generating enzyme. For instance, after the hydrophilic coating is formed on the catheter and prior to placement in contact with the wetting fluid, the hydrophilic coating may be placed into contact with a solution that includes mannose. For example, the catheter including the hydrophilic coating formed thereon may be immersed in a carrier solution of mannose wherein the solution enters the polymer matrix of the hydrophilic coating, thereby carrying the mannose into the matrix to introduce the mannose into the matrix. In other embodiments, the carrier solution may also include the peroxide generating enzyme so that both the mannose and the peroxide generating are carried into and introduced into the matrix of the hydrophilic coating. After a sufficient amount of mannose and, when included peroxide generating enzyme, have been introduced into the coating, the catheter may be removed from the carrier solution and placed in a package. The package may optionally include a wetting solution.

The mannose may also be introduced into the polymer matrix of the hydrophilic coating on a catheter by contacting the coating with a wetting fluid that includes mannose. Optionally, the wetting fluid may also include a peroxide generating enzyme. The catheter may be placed in the package with a wetting fluid that includes mannose. When the wetting fluid wets the hydrophilic coating, it enters the matrix of the hydrophilic coating, carrying mannose with it. When the user removes the catheter for use, the hydrophilic catheter includes mannose therein, and peroxide generating enzyme when one is used, which provides an anti-infective effect during storage and use.

Thus, the present disclosure also relates to a wetting fluid including mannose, a wetting fluid including mannose and a peroxide generating enzyme, and a wetting fluid including a peroxide generating enzyme.

Additionally, the above described catheter assemblies may be sterilized in a suitable manner. For example, the catheter assemblies may be radiation sterilized with gamma or E-beam radiation. Furthermore, any of the packages disclosed above or discussed herein may be gas and liquid impermeable. Alternatively and depending on the application, the packages may be gas permeable.

Mannose and/or Sugar Alcohol Additives for Hydrophilic Formulations and Wetting Fluids The present disclosure also relates to a mannose additive that may be added to a hydrophilic formulation or a wetting fluid. The mannose containing additive may include
  mannose in an amount between about 75 wt % and about 85 wt % of the additive; and
  solvent, such as water, in an amount between about 15 wt % and about 25 wt %.

The additive may also include other agents such as any of the above mentioned organic acids, antioxidants and/or peroxide generating enzyme. When included, the organic acids may be in an amount between about 0.1 wt % and about 8.0 wt % of the additive, the antioxidant may be in an amount between about 0.01 wt % and about 1.0 wt % of the additive, and the peroxide generating enzyme may be in an amount between about 0.0005 wt % and about 0.5 wt % of the coating formulation. In another embodiment, the enzyme may be below 0.01 wt %. In another embodiment, the enzyme could be between about 10 U active units per 100 grams dry weight and about 1400 U active units per 100 grams dry weight. The amount of enzyme may be sufficient to yield between about 10 mg/100 g background hydrogen peroxide in the coating over time and about 25 mg/100 g background hydrogen peroxide in the coating over time. The additive may also include a thixotropic agent, such as one or more of pectin, agar, alginate or the like.

In addition to mannose, or in an alternative to mannose, the additive may include a sugar alcohol, such as 3-carbon sugar alcohols (Glycerol); 4-carbon sugar alcohols (Erythritol, Threitol); 5-carbon sugar alcohols (Arabitol, Xylitol, Ribitol) sugar alcohols, 6-carbon sugar alcohols (Mannitol, Sorbitol, Galactitol, Fucitol, Iditol, Inositol), 7-carbon sugar alcohols (Volemitol), 12-carbon sugar alcohols (Isomalt, Maltitol, Lactitol), 18-carbon sugar alcohols (Maltotriitol), 24-carbon sugar alcohols (Maltotetraitol) and Polyglycitol.

The mannose or sugar alcohol containing additive may be added to a hydrophilic coating formulation that forms a hydrophilic coating. It may be added to a wetting fluid, or may be added to a carrier solution for introducing mannose or sugar alcohol into a hydrophilic coating. Thus, the present disclosure also relates to hydrophilic coatings and wetting fluids containing sugar alcohol or sugar alcohol and an enzyme. In one embodiment, an additive may include a hydrophilic polymer, mannose, and at least one sugar alcohol, such as xylitol for example. Optionally, this additive may also include one or more of inulins (such as, for example, inulin extracted from asteraceae plants or synthetic inulin), at least one peroxide generating enzyme and/or at least one organic acid
  or salts thereof. Furthermore, a hydrophilic coating or a wetting fluid also may include a hydrophilic polymer, mannose, and at least one sugar alcohols, such as xylitol for example. Optionally, this additive may also include one or more of inulins, at least one peroxide generating enzyme and/or at least one organic acid or salts thereof. Similar to as discussed above relative to mannose, the sugar alcohol or additives, such as those mentioned above, can be included in the coating by addition to the coating formulation that forms the coating or by infiltration into an already formed coating.

Hydrophilic Coatings and Wetting Fluids Containing Honey

Hygienic hydrophilic coatings of the present disclosure may include a hydrophilic polymer, honey (natural or synthetic) and, optionally, other additives and agents. As used herein natural honey refers to honey made naturally by bees (whether considered active or not) and synthetic honey refers to substances that include substantially the same components of natural honeys but are man-made.

The hygienic hydrophilic coating may include
  hydrophilic polymer(s) in an amount between about 70 wt % and about 99 wt % of the coating; and
  honey in an amount between about 1 wt % and about 30 wt % of the coating.

In one embodiment, the hygienic hydrophilic coating may include
  hydrophilic polymer(s) in an amount between about 80 wt % and about 98 wt % of the coating; and
  honey in an amount of about 2 wt % and about 20 wt %.

The hygienic hydrophilic coating may optionally include other agents or additives, such as any of the above-mentioned organic acids, antioxidants and/or peroxide generating enzyme. The organic acids may be in an amount between about 0.01 wt % and about 8.0 wt % of the coating. The antioxidants may be in an amount between about 0.01 wt % and about 1.0 wt % of the coating. The peroxide generating enzyme may be in an amount between about 0.0005 wt % and about 0.5 wt % of the coating. In another embodiment, the enzyme may be below 0.01 wt %. In another embodiment, the enzyme could be between about 10 U active units per 100 grams dry weight and about 1400 U active units per 100 grams dry weight. The amount of enzyme may be sufficient to yield between about 10 mg/100 g background hydrogen peroxide in the coating over time and about 25 mg/100 g background hydrogen peroxide in the coating over time.

The honey may be an inherently active honey that generates a background level of hydrogen peroxide. Alternatively, when a peroxide generating enzyme is included in the coating, such enzyme may catalyse the saccharides of the honey to generate peroxide, such as hydrogen peroxide. The amount of peroxide generating enzyme may be sufficient so that the catalyzation may generate peroxide over a relatively long period of time, resulting in a continuous release of peroxide that can provide anti-infective protection during storage and use of the catheter.

The hydrophilic coating containing honey may be formed from a hydrophilic coating formulation, such as a solution or dispersion, containing the hydrophilic polymer(s), honey and, optionally, other agents/additives. The hydrophilic coating formulation may be applied to the catheter shaft by any of the above discussed procedures. Depending on the desired coating, the coating formulation may then be dried and/or cured to form the hydrophilic coating on the catheter. The hydrophilic coating may be formed directly on the surface of the catheter shaft or over a base/tie coating layer as described above.

In one embodiment, the hydrophilic coating formulation may include
  hydrophilic polymer(s) in an amount between about 80 wt % and about 97 wt % of the coating formulation;
  honey in an amount between about 1 wt % and about 20 wt % of the coating formulation; and
  a solvent in an amount between about 80 wt % and about 99 wt % of the coating formulation.
The solvent may be, for example, water, ethanol, methanol or any combination thereof or any other suitable solvent. The curing agent may be, for example, benzophenone.

The hydrophilic coating formulation may, optionally, also include an additional effective amount of a peroxide generating enzyme that is effective to catalyse the saccharides of the honey to generate peroxide. In one embodiment, the peroxide generating enzyme may be in an amount between about 0.05 wt % and about 0.5 wt % of the coating formulation. In another embodiment, the enzyme may be below 0.01 wt %. In other embodiments, the enzyme could be between about could be 5 U active units per 100 grams dry weight of the other components of the coating and about 4000 U actives units per 100 grams dry weight. The amount of enzyme may be sufficient to yield between about 10 mg/100 g background hydrogen peroxide in the coating over time and about 25 mg/100 g background hydrogen peroxide in the coating over time. In another embodiment, the enzyme could be between about 10 U active units per 100 grams dry weight and about 1400 U active units per 100 grams dry weight. The coating may also optionally include any of the above mentioned curing agents. The curing agent may be in an amount between about 0.1 wt % and about 1.0 wt %. The coating formulation may also optionally include an organic acid in an amount between about 0.01 wt % and about 8.0 wt %, and/or an antioxidant in an amount between about 0.05 wt % and about 1.0 wt %. The coating formulation may also optionally include any other suitable agents/additives, such as plasticizers, humectants, compounds that aid in attachment of the coating to a surface, and/or polyelectrolytes.

In one embodiment, the coating formulation may include
  hydrophilic polymer(s), such as PVP, in an amount between about 0.9 wt % and about 20 wt % of the coating formulation;
  honey in an amount between about 0.5 wt % and about 5.0 wt % of the coating formulation;
  curing agent in an amount between about 0.1 wt % and about 1.0 wt % of the coating formulation;
  peroxide generating enzyme, such as glucose oxidase, in an amount between 0.0005 wt % and about 0.5 wt % of the coating formulation; or the enzyme may be below 0.01 wt %; or the enzyme could be between about could be 5 U active units per 100 grams dry weight of the other components of the coating and about 1400 U active units per 100 grams dry weight. The amount of enzyme may be sufficient to yield between about 10 mg/100 g background hydrogen peroxide in the coating over time and about 25 mg/100 g background hydrogen peroxide in the coating over time; and
  solvent in an amount between about 73 wt % and about 98.5 wt % of the coating formulation.

Once the coating is formed on the catheter, the catheter may be packaged in a catheter assembly for storage, distribution and use by the end-user. The catheter assembly may include a package that contains the catheter and a wetting fluid that wets the hydrophilic coating to render it lubricious. The wetting fluid may include any suitable wetting agent that wets the hydrophilic coating. The wetting agent may be for example, water or saline. The hydrophilic coated catheter may be packaged in contact with the wetting fluid or the package may include separate compartments for the catheter and the wetting fluid wherein the compartments are brought into communication during the manufacturing process or just prior to use by the user.

In one embodiment, the catheter assembly includes a package having therein a catheter including a hydrophilic coating that has a hydrophilic polymer, honey and, optionally, any of the above-mentioned additives/agents. In another embodiment, the package includes therein a catheter having a hydrophilic coating that has a hydrophilic polymer, honey, a peroxide generating enzyme and, optionally, any other of the above-mentioned additives/agents.

In yet another embodiment the catheter within the package may include a hydrophilic coating that has a hydrophilic polymer and honey. The package also includes a wetting fluid that includes a wetting agent, such as water or saline, and a peroxide generating enzyme. In this embodiment, when the wetting fluid wets the hydrophilic coating and enters the matrix of the hydrophilic coating, the peroxide generating enzyme will enter the matrix and catalyze the saccharides of the honey to generate peroxide while the catheter is stored within the package and during use by the user.

In yet another embodiment, the catheter may include may include a hydrophilic coating that does not include any honey when the coating is formed. Honey may be introduced into the coating by contacting the coating with a fluid that includes honey. Optionally, the fluid may also include a peroxide generating enzyme. For instance, after the hydrophilic coating is formed and prior to placement in contact with the wetting fluid, the hydrophilic coating may be placed into contact with a solution that includes honey. For example, the catheter including the hydrophilic coating formed thereon may be immersed in a carrier solution including honey wherein the solution enters the polymer matrix of the hydrophilic coating, thereby carrying the components of the honey into the matrix to introduce the honey components into the matrix. In other embodiments, the carrier solution may also include the peroxide generating enzyme so that both the honey and the peroxide generating are carried into and introduced into the hydrophilic coating. After a sufficient amount of honey and, when included peroxide generating enzyme, have been introduced into the coating, the catheter may be removed from the carrier solution and placed in a package. The package may optionally include a wetting solution.

The honey may also be introduced into the polymer matrix of the hydrophilic coating on a catheter by contact with a wetting fluid that includes honey. Optionally, the wetting fluid may also include a peroxide generating enzyme. The catheter may be placed in the package with a wetting fluid that includes honey. When the wetting fluid wets the hydrophilic coating, it enters the matrix of the hydrophilic coating, carrying the honey components with it.

When the user removes the catheter for use, the hydrophilic catheter includes honey therein, and peroxide generating enzyme when one is used, which provides an anti-infective effect during storage and use.

Thus, the present disclosure also relates to a wetting fluid including honey and a wetting fluid including honey and a peroxide generating enzyme.

Additionally, the above described catheter assemblies may be sterilized in a suitable manner. For example, the catheter assembly may be radiation sterilized with gamma or E-beam radiation.

Hydrophilic Coatings and Wetting Fluids Containing Alcohol

Hygienic hydrophilic coatings of the present disclosure may include a hydrophilic polymer and an alcohol(s). In one embodiment, the coating may include blends of C12 to C22 alcohol and C12 to C22 alcohol ethoxylate. In another embodiment, the coating may include an aromatic alcohol(s), such as one or more of phenoxyethanol, benzyl alcohol and phenylethyl alcohol.

The hydrophilic coating may also optionally include other additives and agents.

The hygienic hydrophilic coating may include
hydrophilic polymer(s) in an amount between about 80 wt % and about 99.6 wt % of the coating; and
combined amounts of C12 to C22 alcohol and C12 to C22 alcohol ethoxylate may be between about 0.4 wt % and about 20.0 wt % of the coating.

In one embodiment, the hygienic hydrophilic coating may include
hydrophilic polymer(s) in an amount between about 95 wt % and about 99.9 wt % of the coating; and
combined amounts of C12 to C22 alcohol and C12 to C22 alcohol ethoxylate may be about 0.1 wt % and about 5.0 wt % of the coating.

The ratio of C12 to C22 alcohol to C12 to C22 alcohol ethoxylate in the coating may be about 10:90 or 90:10, respectively, and in one embodiment is 70:30.

In another embodiment, the hygienic hydrophilic coating may include
hydrophilic polymer(s) in an amount between about 95 wt % and about 99.9 wt % of the coating; and
aromatic alcohol(s) may be between about 0.1 wt % and about 5.0 wt % of the coating.

Optionally, the hygienic hydrophilic coating including an alcohol may also include other agents or additives, such as the above mentioned organic acids and antioxidants. The organic acids, or mixture of organic acids, may be in an amount between about 0.01 wt % and about 8.0 wt % of the coating. The antioxidants may be in an amount between about 0.05 wt % and about 1.0 wt % of the coating.

The hydrophilic coating containing C12 to C22 alcohol and/or C12 to C22 alcohol ethoxylate may be formed from a hydrophilic coating formulation, such as a solution or dispersion containing the hydrophilic polymer(s), C12 to C22 alcohol and/or C12 to C22 alcohol ethoxylate and optionally, other agents/additives of the coating. The hydrophilic coating containing an aromatic alcohol(s) likewise may be formed from a hydrophilic coating formulation containing hydrophilic polymer(s), aromatic alcohol and optionally, other agents/additives of the coating. The hydrophilic coating formulation may be applied to the catheter shaft by of the above-mentioned coating procedures. Depending on the desired coating, the coating formulation may then be dried and/or cured to form the hydrophilic coating on the catheter. The hydrophilic coating may be formed directly on the surface of the catheter shaft or over a base/tie coating layer as described above.

In one embodiment, the hydrophilic coating formulation may include
hydrophilic polymer(s) in an amount between about 0.9 wt % and about 20 wt % of the coating formulation;
combined amounts of C12 to C22 alcohol and C12 to C22 alcohol ethoxylate may be between about 0.1 wt % and about 5.0 wt % of the coating formulation; and
a solvent in an amount between about 75 wt % and about 99 wt % of the coating formulation.

In another embodiment, the hydrophilic coating formulation may include
hydrophilic polymer(s) in an amount between about 0.9 wt % and about 20 wt % of the coating formulation;
an aromatic alcohol(s) that may be in an amount between about 0.1 wt % and about 5.0 wt % of the coating formulation; and
a solvent in an amount between about 75 wt % and about 99 wt % of the coating formulation.

The solvent may any of those mentioned above or any solvent that is suitably miscible with the alcohol/ethoxylate alcohol and the hydrophilic polymer.

Optionally, the coating formulation may include a curing agent, such as any of those mentioned above, in an amount between about 0.1 wt % and about 1.0 wt % of the coating formulation. The coating formulation may also optionally include an organic acid in an amount between about 0.01 wt % and about 8.0 wt %, and/or an antioxidant in an amount between about 0.05 wt % and about 1.0 wt %. The coating formulation may also optionally include any other suitable agents/additives, such as plasticizers, humectants, compounds that aid in attachment of the coating to a surface, and/or polyelectrolytes.

In one embodiment, the coating formulation may include
hydrophilic polymer(s), such as PVP, in an amount between about 0.9 wt % and about 20.0 wt % of the coating formulation;
combined amounts of C12 to C22 alcohol and C12 to C22 alcohol ethoxylate may be between about 0.1 wt % and about 5.0 wt % of the coating formulation;
curing agent in an amount between about 0.1 wt % and about 1.0 wt % of the coating formulation; and
a solvent in an amount between about 80 wt % and about 99 wt % of the coating formulation.

The ratio of C12 to C22 alcohol to C12 to C22 alcohol ethoxylate in formulation may be about 10:90 or 90:10, respectively, and in one embodiment is 70:30.

In another embodiment, the coating formulation may include
hydrophilic polymer(s), such as PVP, in an amount between about 0.9 wt % and about 20 wt % of the coating formulation;
an aromatic alcohol(s) that may be in an amount between about 0.1 wt % and about 5.0 wt % of the coating formulation;
curing agent in an amount between about 0.1 wt % and about 1.0 wt % of the coating formulation; and
a solvent in an amount between about 80 wt % and about 99 wt % of the coating formulation.

Once the coating is formed on the catheter, the catheter may be packaged in a catheter assembly for storage, distribution and use by the end-user. The catheter assembly may include a package that contains the catheter and a wetting fluid that wets the hydrophilic coating to render it lubricious. The wetting fluid may include any suitable wetting agent that wets the hydrophilic coating. The wetting agent may be for example, water or saline. The hydrophilic coated catheter may be packaged in contact with the wetting fluid or the package may include separate compartments for the catheter and the wetting fluid wherein the compartments are brought into communication during the manufacturing process or just prior to use by the user.

In one embodiment, the catheter within the package of the catheter assembly may include a hydrophilic coating that has a hydrophilic polymer, C12 to C22 alcohol and C12 to C22 alcohol ethoxylate or an aromatic alcohol and, optionally, any of the above-mentioned additives/agents.

In yet another embodiment, the catheter may include a hydrophilic coating that does not include any alcohol(s), such as C12 to C22 alcohol, C12 to C22 alcohol ethoxylate or aromatic alcohol when the coating is formed. The alcohol may be introduced into the coating by contacting the coating with the alcohol, which may be in a solution. For instance, after the hydrophilic coating is formed and prior to placement in contact with the wetting fluid, the hydrophilic coating may be placed into contact with C12 to C22 alcohol and C12 to C22 alcohol ethoxylate and in another embodiment with the hydrophilic coating may be placed into contact with an aromatic alcohol(s). In one embodiment, the catheter including the hydrophilic coating formed thereon may be immersed in a solution of C12 to C22 alcohol and C12 to C22 alcohol ethoxylate. In another embodiment, the catheter including the hydrophilic coating may be immersed in a solution containing aromatic alcohol. The solution enters the polymer matrix, thereby carrying the alcohol into the matrix to introduce alcohol into the matrix. After a sufficient amount of alcohol has been introduced into the matrix of the hydrophilic coating, the catheter may be removed from the solution and placed in a package. Optionally, the package may include a wetting fluid.

Alcohol may also be introduced into the polymer matrix of the hydrophilic coating on a catheter by contact with a wetting fluid that includes alcohol. Such a wetting fluid may include a wetting agent that activates the lubriciousness of the hydrophilic coating and is miscible with the alcohol/alcohol ethoxylate or aromatic alcohol. The wetting agent may be, for example, water or glycerol. In one embodiment, the catheter may be placed in the package with a wetting fluid that includes C12 to C22 alcohol and C12 to C22 alcohol ethoxylate. In another embodiment, the catheter may be placed in the package with a wetting fluid that includes aromatic alcohol(s). When the wetting fluid wets the hydrophilic coating, it enters the matrix of the hydrophilic coating, carrying the alcohol with it into the matrix. When the user removes the catheter for use, the hydrophilic catheter includes alcohol therein, which provides an anti-infective effect.

Thus, the present disclosure also relates to a wetting fluid including C12 to C22 alcohol and C12 to C22 alcohol ethoxylate and wetting fluids include aromatic alcohol.

Examples

Hydrophilic coatings were formed on the outer surfaces of catheters made from polyvinyl chloride (PVC catheters). The catheters had a size of CH14 and a shore hardness of 82A. The hydrophilic coatings included a base coat layer formed on the outer surface of the catheter and a top coat layer formed over the base coat layer. The base coat composition was prepared as indicated below. The base coat composition was applied to the outer surface of each of the catheters and then cured and dried to form a base coat layer thereon.

The base coat composition included the following components:

| Base Coat Composition | |
|---|---|
| Component | Amount |
| Methanol | 97.98% (w/w) |
| Polyvinylpyrrolidone K90 (PVP) (Ashland) | 1.61% (w/w) |
| Irgacure 2959 (BASF) | 0.01% (w/w) |
| Polyethylene glycol diacrylate (PEG400DA) (SR344, Sartomer, inhibitor removed) | 0.40% (w/w) |

The base coat composition was prepared by slowly adding the PVP to methanol while mixing until the PVP was dissolved. PEG400DA and Irgacure 2959 were then added and allowed to fully dissolve while the solution was stirred.

Top coat compositions were prepared with the components as shown in the table below. Each of the catheters had one of the top coat compositions applied over the base coat layer. The top coat compositions were then cured and dried to form a hydrophilic coating on the outer surface of the catheter.

The formulations of the top coat compositions were as follows:

| | Top Coats | | | | |
|---|---|---|---|---|---|
| | Top Coat 1 | Top Coat 2 | Top Coat 3 | Top Coat 4 | Top Coat 5 |
| Ethanol (Absolute) | 62.41 g | 62.41 g | 62.41 g | 62.41 g | 62.41 g |
| De-ionized water | 14.00 g | 14.00 g | 14.00 g | 14.00 g | 14.00 g |
| PVP K90 (Ashland) | 5.95 g | 5.95 g | 5.95 g | 5.95 g | 5.95 g |
| BHT-A (Sigma Aldrich) | 0.01 g | 0.01 g | 0.01 g | 0.01 g | 0.01 g |
| PEG400DA (SR344, Sartomer) | 0.30 g | 0.30 g | 0.30 g | 0.30 g | 0.30 g |
| Glycerol (Sigma Aldrich) | 0.73 g | 0.73 g | 0.73 g | 0.73 g | 0.73 g |
| Benzophenone (Sigma Aldrich) | 0.01 g | 0.01 g | 0.01 g | 0.01 g | 0.01 g |
| d-Mannose (Sigma Aldrich) | 0.20 g | 2.00 g | — | — | — |
| Xylitol (Sigma Aldrich) | — | — | 0.20 g | 2.00 g | — |
| Natural Honey (Boyne Valley) | — | — | — | — | 5.0 g |

Each of the top coat compositions were prepared by adding PVP to the ethanol and water and mixing until dissolved. The BHT-A, PEG400DA, glycerol, and benzophenone were then added and allowed to fully dissolve under stirring. Finally, d-mannose, Xylitol and Natural Honey, were added to the respective coating formulation and allowed to fully dissolve under stirring.

To form the hydrophilic coating on the outer surfaces of each of the catheters, the catheters were immersed in the base coat composition for a period of 10 seconds and then withdrawn at a rate of 0.7 cm/sec using a Harland PCX coating machine containing UV lamps. The base coat composition was then cured and dried under UV lamps for 45 seconds to form a base coat layer covering the outer surface of the catheter. The catheters were then immersed into one of the five top coat compositions for 10 seconds and withdrawn at a rate of 0.5 cm/sec. The top coat composition was then UV cured and dried under UV lamps for 10 minutes to form the top coat layer resulting in the formation of a hydrophilic coating on the catheter.

Catheters coated with each of the formulations were divided into two groups. The first group was tested in an unsterilized state and the second group was packaged in aluminium foil pouches, sealed and sterilized by gamma irradiation in the package at 30-35 kGy.

The unsterilized and sterilized initial and abraded coefficients of friction (CoFs) of catheter including Top Coats 1-4 were measured with the hydrophilic coating in a hydrated state. The sterilized initial, abraded and ten minute dry-out coefficients of friction (CoFs) of catheters including Top Coat 5 were also tested. When testing the CoFs, the catheters were immersed in water for 30 seconds to achieve a hydrated state. Additionally, a ten minute dry-out time CoF was measured for Top Coat 5.

CoF measurements are an indicator of lubricity and were measured using a Harland Friction Tester Model FTS5500. The CoFs of the catheters were determined by inserting a mandrel into 127 mm section of the coated catheter tube. The tube was then clamped between two pieces of silicone rubber at 100 g load wherein the silicone rubber had a shore hardness of 60A. The catheter tube with the mandrel inserted therein was pulled through the two pieces of silicone rubber at a speed of 10 mm/s. The force required to pull about 80 mm of the catheter tube through the two pieces of silicone rubber was measured. The CoF value was calculated from the ratio of recorded to applied loads (i.e., the recorded load divided by the applied load) when steady state was reached. The CoF of each type of catheter was measured immediately after hydration ("initial"), immediately after being abraded ("abraded") and immediately after a ten-minute dry-out time ("dry-out").

In measuring the abraded CoFs, the catheter, with the hydrophilic coating in a hydrated state, was cycled back and forth 25 times through a hole in a 1 mm thick, silicone pad having a shore hardness of 60A. The hole was just smaller than the outer diameter of the catheter tube and the abrasion took place under water. Abrading the catheter in this fashion is designed to remove any portions of the coating that is not well adhered to the tubes. After abrasion, the CoF was measured as described above.

In measuring the ten minute dry-out time CoF, the catheter, immediately after hydration for "dry sterilized" catheter or immediately after removal from the package for "wet sterilized" catheters, was placed in an atmosphere having a temperature of 23° C. and a relative humidity of 50% for 10 minutes before measuring the CoF.

Results

Coefficient of Friction Measurements

Table 1 shows the average CoFs for the initial and abraded CoFs for unsterilized and sterilized catheters coated with Top Coats 1-4.

TABLE 1

| | Unsterilized | | Sterilized | |
| --- | --- | --- | --- | --- |
| | Initial CoF Avg. | Abraded CoF Avg. | Initial CoF Avg. | Abraded CoF Avg. |
| Top Coat 1 | 0.0253 | 0.0276 | 0.0166 | 0.0175 |
| Top Coat 2 | 0.0215 | 0.0259 | 0.0135 | 0.0187 |

TABLE 1-continued

| | Unsterilized | | Sterilized | |
| --- | --- | --- | --- | --- |
| | Initial CoF Avg. | Abraded CoF Avg. | Initial CoF Avg. | Abraded CoF Avg. |
| Top Coat 3 | 0.0227 | 0.0200 | 0.0190 | 0.0192 |
| Top Coat 4 | 0.0301 | 0.0248 | 0.0127 | 0.0143 |

Table 2 shows the average CoFs for the initial, abraded and ten minute dry out CoFs for sterilized catheters coated with Top Coats 5.

TABLE 2

| | Dye Uptake Tests | | |
| --- | --- | --- | --- |
| | Sterilized | | |
| | Initial CoF Avg. | Abraded CoF Avg. | 10 Min Dry-out Avg. |
| Top Coat 5 | 0.0122 | 0.0132 | 0.0143 |

Dye uptake tests were conducted on the catheters post abrasion to assess the coating integrity and the level of adhesion/non-adhesion between the hydrophilic coatings and catheters. After the CoFs of the abraded catheters were measured, the catheters were dried-out (dehydrated). The dried-out catheters were then immersed in a water soluble red dye for 2 minutes. The catheters were then visually inspected to determine if the dye had been uniformly taken up throughout the coating or if sections of the coated portion of the catheter were dye-free. A uniform dye uptake throughout the coated portion of the catheter indicates that the hydrophilic coating has good integrity and good adhesion to the catheter. If the coated portion of the catheter has undyed sections, this is an indication that the hydrophilic coating or sections thereof have significantly thinned and/or separated from the catheter due to lack of adhesion to the catheter.

Figure 2:
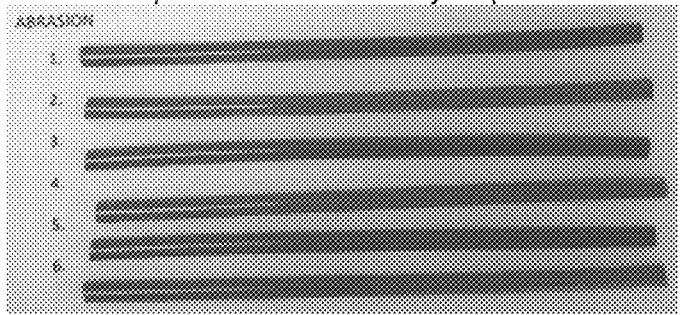
Figure 3:
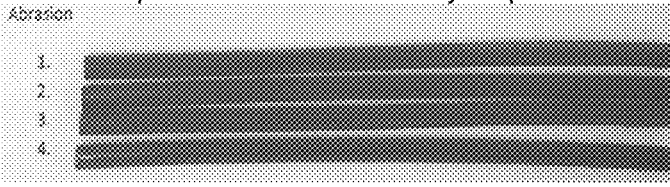
FIGS. 3 and 4 are photographs of catheter tubes showing the visual results of the dye uptake tests of Top Coat 2.
Figure 4:
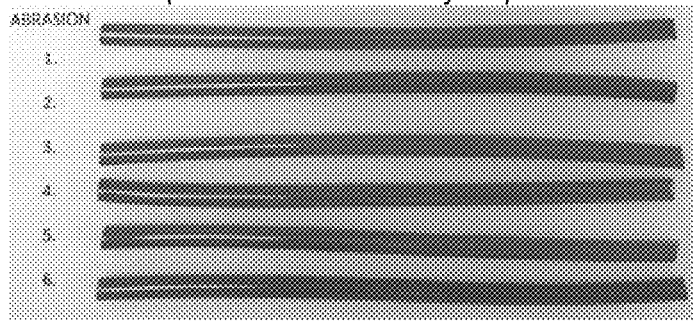
Figure 5:
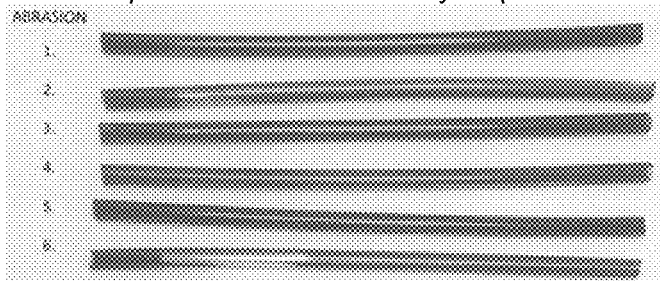
FIGS. 5 and 6 are photographs of catheter tubes showing the visual results of the dye uptake tests of Top Coat 3.
Figure 6:
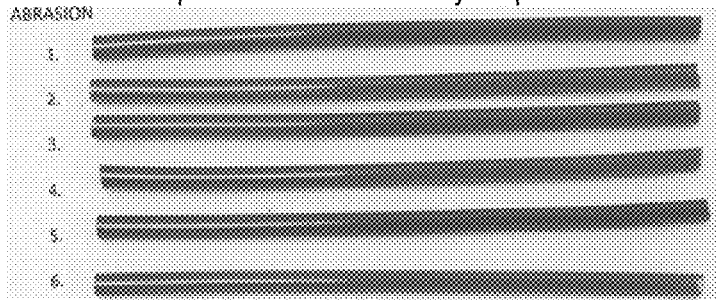
Figure 7:
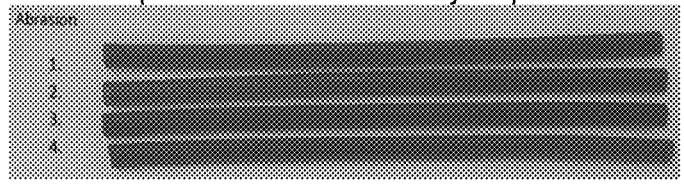
FIGS. 7 and 8 are photographs of catheter tubes showing the visual results of the dye uptake tests of Top Coat 4.
Figure 8:
Figure 9:
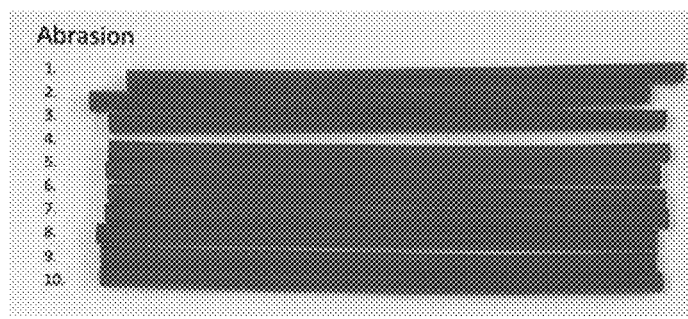
FIG. 9 is a photograph of catheter tubes showing the visual results of the dye uptake tests of Top Coat 5.

Referring to FIGS. 1-9, visual inspection of catheters including hydrophilic coatings formed from Top Coats 1 through Top Coat 5, sterilized and unsterilized, show that the hydrophilic coatings exhibited uniform dye uptake which is an indication that the hydrophilic coating had strong adhesion to the catheter and good coating cohesion.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:
1. A lubricous hydrophilic catheter assembly, comprising:
a gas impermeable and liquid impermeable package having a sealed cavity;
a catheter having a hydrophilic coating located within the sealed cavity; and
a wetting fluid comprising a wetting agent and mannose located within the sealed cavity.

2. The catheter assembly of claim 1, wherein the wetting fluid further includes a peroxide generating enzyme.

3. The catheter assembly of claim 2, wherein the enzyme comprises an oxidoreductase.

4. The catheter assembly of claim 2, wherein the enzyme comprises glucose oxidase.

5. The catheter assembly of claim 2, wherein the enzyme comprises peroxidase.

6. The catheter assembly of claim 5 wherein the peroxidase comprises lactoperoxidase.

7. The catheter assembly of claim 1, wherein the hydrophilic coating comprises a hydrophilic polymer matrix.

8. The catheter assembly of claim 7, wherein a hydrophilic polymer of the hydrophilic polymer matrix comprises polyvinylpyrrolidone.

9. The catheter assembly of claim 1, wherein the hydrophilic coating further comprises an antioxidant.

10. The catheter assembly of claim 1 wherein the hydrophilic coating further comprises a thixotropic agent.

11. The catheter assembly of claim 10 wherein the thixotropic agent comprises pectin, agar and/or alginate.

12. The catheter assembly of claim 1 wherein the wetting fluid further comprises sugar alcohol.

13. The catheter assembly of claim 12, wherein the sugar alcohol is xylitol.

14. The catheter assembly of claim 1 wherein the hydrophilic coating or wetting fluid further comprises an organic acid.

15. A method of forming a lubricous hydrophilic catheter assembly, comprising:
   inserting a catheter having a hydrophilic coating into a gas impermeable and liquid impermeable package having a cavity;
   placing a wetting fluid into the cavity, wherein the wetting fluid comprises a wetting agent and mannose; and
   sealing the cavity.

16. The method of claim 15, further comprising sterilizing the catheter assembly.

17. The method of claim 16, wherein the sterilizing is radiation sterilization.

18. The method of claim 17, wherein the radiation sterilization is gamma or E-beam radiation.

19. The method of claim 15, wherein the catheter is inserted into the package in contact with the wetting fluid.

20. The method of claim 15, wherein the catheter is inserted into a package in a separate compartment from the wetting fluid.

21. The method of claim 20, wherein the compartments are brought into communication just prior to use by a user.

22. The method of claim 15, wherein the hydrophilic coating comprises a hydrophilic polymer matrix.

23. The method of claim 22, wherein a hydrophilic polymer of the hydrophilic polymer matrix comprises polyvinylpyrrolidone.

\* \* \* \* \*